(12) United States Patent
Nering et al.

(10) Patent No.: US 10,368,860 B2
(45) Date of Patent: Aug. 6, 2019

(54) ABSORBABLE SURGICAL FASTENERS FOR SECURING PROSTHETIC DEVICES TO TISSUE

(71) Applicant: Ethicon, Inc., Somerville, NJ (US)

(72) Inventors: Robert Nering, Stockton, NJ (US); Glenn Cook, Clinton, NJ (US); James A. Flint, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 228 days.

(21) Appl. No.: 14/549,984

(22) Filed: Nov. 21, 2014

(65) Prior Publication Data

US 2016/0143637 A1    May 26, 2016

(51) Int. Cl.
| *A61B 17/064* | (2006.01) |
| *A61B 17/068* | (2006.01) |
| *A61F 2/00* | (2006.01) |
| *A61B 17/10* | (2006.01) |
| *A61B 17/00* | (2006.01) |

(52) U.S. Cl.
CPC .......... *A61B 17/064* (2013.01); *A61B 17/068* (2013.01); *A61B 17/10* (2013.01); *A61B 2017/00004* (2013.01); *A61B 2017/0641* (2013.01); *A61F 2/0063* (2013.01); *A61F 2220/0016* (2013.01)

(58) Field of Classification Search
CPC .................. A61B 17/064; A61B 17/10; A61B 2017/00004; A61B 2017/0641; B65D 33/1641; F16B 15/00; F16B 15/0015
USPC ........................................................ 606/151
See application file for complete search history.

(56) References Cited

U.S. PATENT DOCUMENTS

| D205,375 S | 7/1966 | Marotz |
| 4,548,202 A | 10/1985 | Duncan |
| D298,916 S | 12/1988 | Beatty |
| 4,932,960 A | 6/1990 | Green |
| 5,223,675 A | 6/1993 | Taft |
| 5,258,012 A | 11/1993 | Luscombe |
| 5,314,427 A | 5/1994 | Goble |
| 5,478,354 A | 12/1995 | Tovey et al. |
| D377,754 S | 2/1997 | Abbott |
| D378,409 S | 3/1997 | Michelson |
| 5,649,937 A | 7/1997 | Bito et al. |
| 5,797,932 A | 8/1998 | Min et al. |
| 5,830,221 A | 11/1998 | Stein et al. |
| 6,187,009 B1 | 2/2001 | Herzog et al. |

(Continued)

FOREIGN PATENT DOCUMENTS

| EP | 1437968 | 7/2004 |
| FR | 2980966 | 4/2013 |
| WO | 2011046982 | 4/2011 |

OTHER PUBLICATIONS

International Search Report from corresponding International Application No. PCT/US2015/060983, dated Jan. 4, 2016, 5 pages.

*Primary Examiner* — George J Ulsh

(57) ABSTRACT

A surgical fastener for anchoring medical devices to tissue includes first and second legs lying in a first plane, and third and fourth legs lying in a second plane that is orthogonal with the first plane. A bridge interconnects proximal ends of the four legs for forming a closed end of the surgical fastener. Each leg has a proximal end, a distal end, and an insertion tip with a distal point located at the distal end of the leg. Each leg has an insertion tool alignment guide that extends between the proximal and distal ends of the leg and along a longitudinal axis that is aligned with the distal point of the insertion tip.

21 Claims, 16 Drawing Sheets

(56) References Cited

U.S. PATENT DOCUMENTS

| | | |
|---|---|---|
| 6,447,524 B1 | 9/2002 | Knodel et al. |
| 6,517,566 B1 | 2/2003 | Hovland et al. |
| 7,267,682 B1 | 9/2007 | Bender |
| 7,867,252 B2 | 1/2011 | Criscuolo et al. |
| 8,114,099 B2 | 2/2012 | Shipp |
| 8,292,154 B2 | 10/2012 | Marczyk |
| 8,518,055 B1 | 8/2013 | Cardinale |
| 8,579,920 B2 | 11/2013 | Nering et al. |
| 8,585,721 B2 | 11/2013 | Kirsch |
| D698,021 S | 1/2014 | Nering |
| 8,663,244 B2 | 3/2014 | Reeser |
| D744,646 S | 12/2015 | Nering |
| 2002/0029064 A1 | 3/2002 | Kanner |
| 2002/0169465 A1 | 11/2002 | Bowman et al. |
| 2006/0129152 A1 | 6/2006 | Shipp |
| 2007/0162030 A1 | 7/2007 | Aranyi et al. |
| 2007/0270906 A1 | 11/2007 | Molz |
| 2009/0030434 A1 | 1/2009 | Paz et al. |
| 2010/0292715 A1 | 11/2010 | Nering |
| 2011/0087277 A1 | 4/2011 | Viola et al. |
| 2011/0106113 A1 | 5/2011 | Tavakkolizadeh et al. |
| 2012/0029538 A1 | 2/2012 | Reeser |
| 2013/0218177 A1 | 8/2013 | Miksza |
| 2013/0331867 A1 | 12/2013 | Reeser et al. |
| 2015/0230839 A1 | 8/2015 | Riccione |

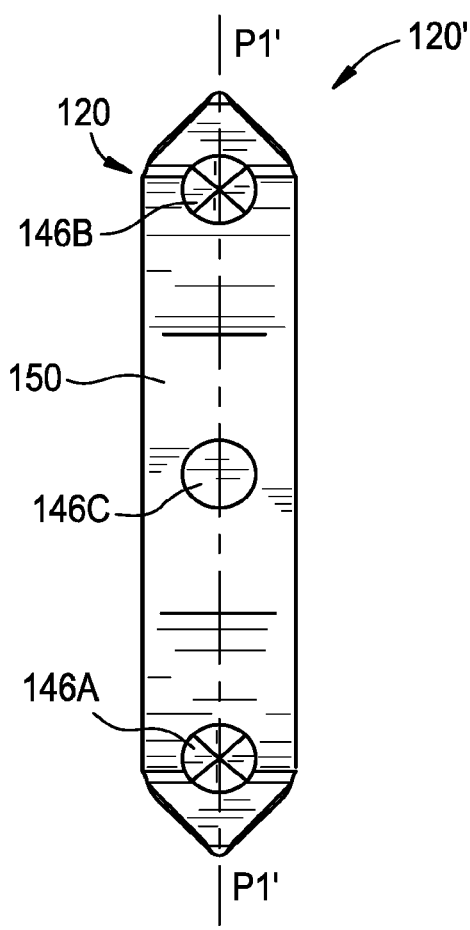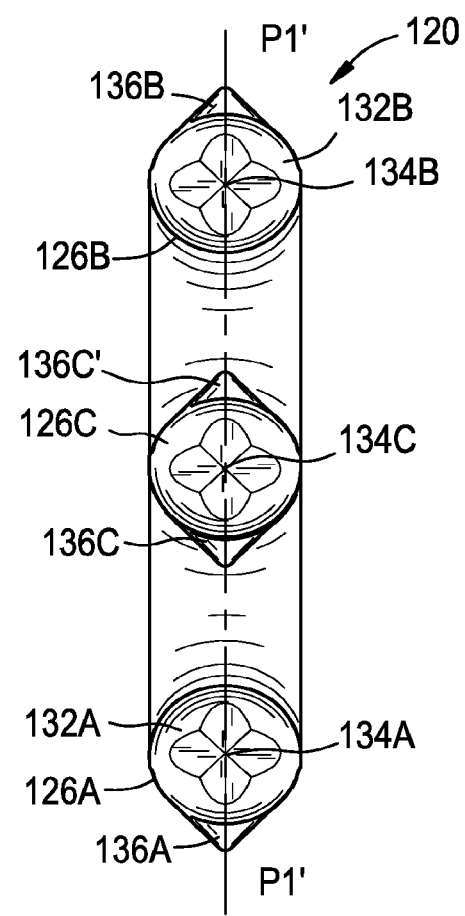

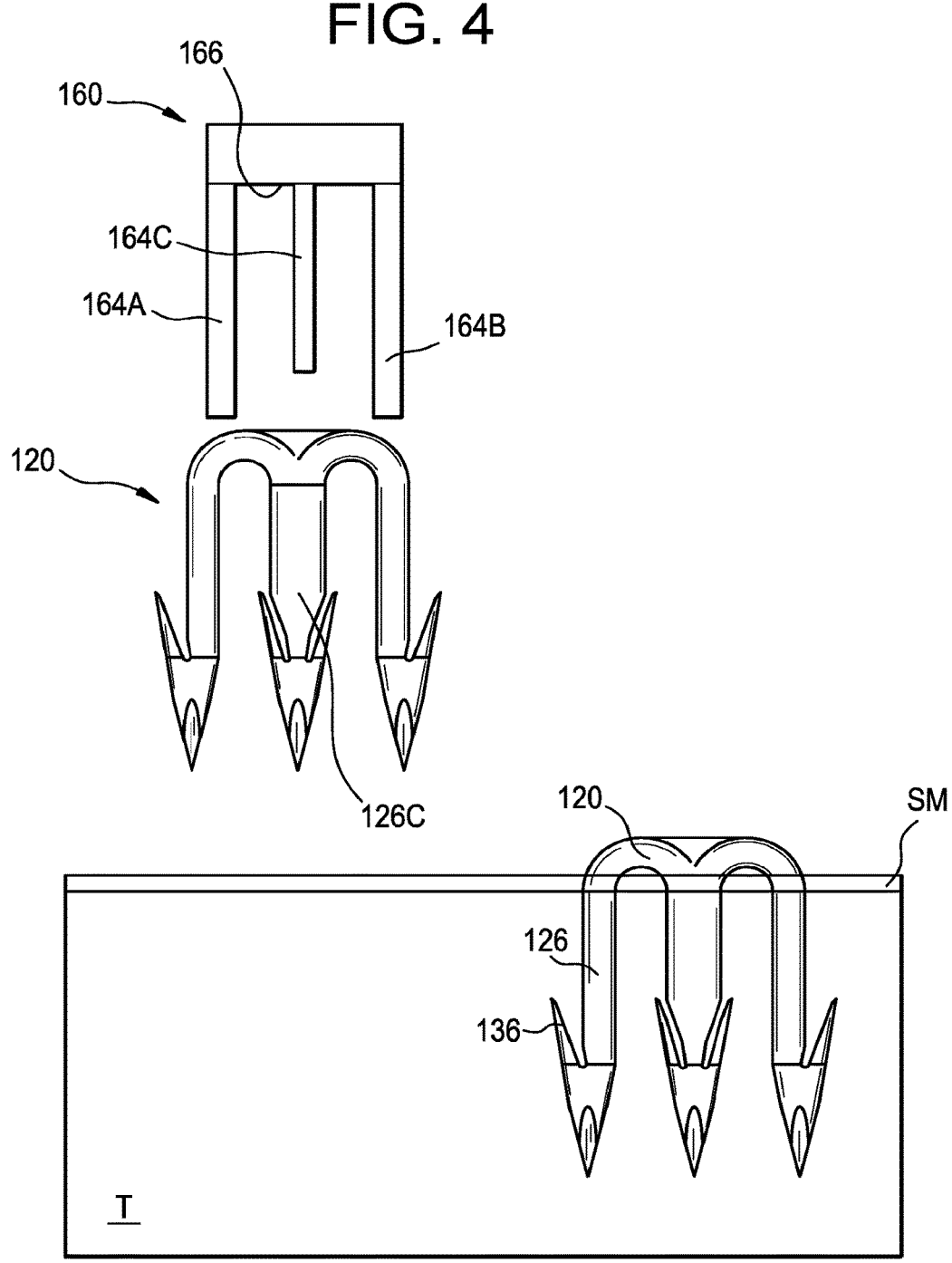

FIG. 6
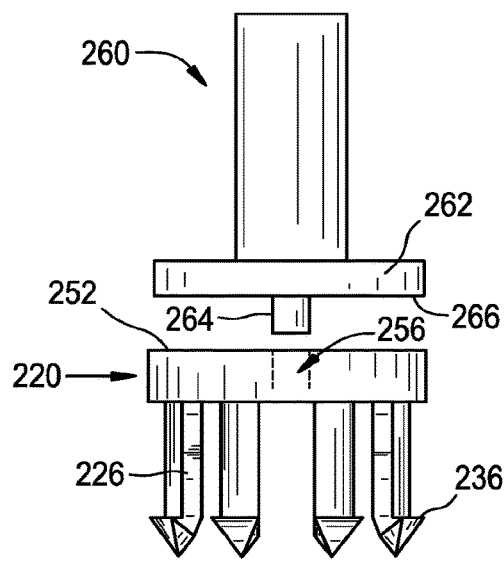
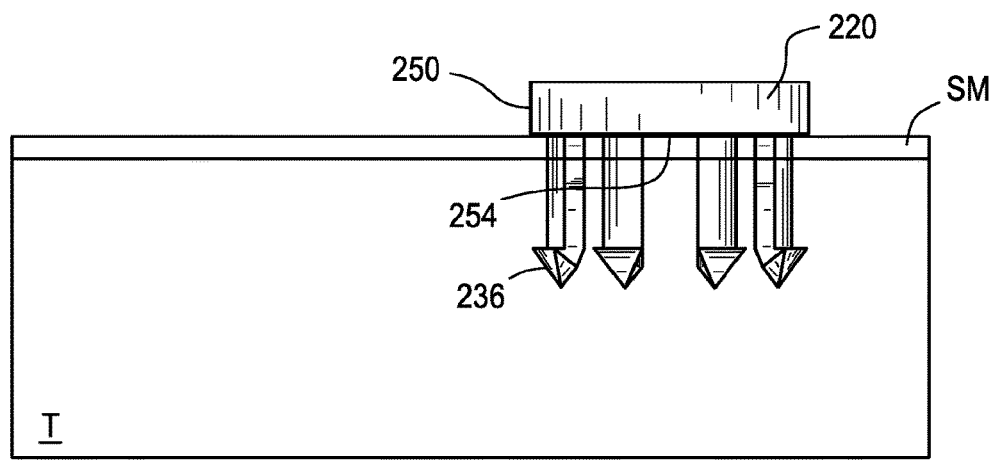

ABSORBABLE SURGICAL FASTENERS FOR SECURING PROSTHETIC DEVICES TO TISSUE

BACKGROUND OF THE INVENTION

Field of the Invention

The present invention generally relates to surgical fasteners, and more specifically relates to absorbable surgical fasteners for securing prosthetic devices such as surgical mesh to tissue.

Description of the Related Art

Hernia is a condition whereby a small loop of bowel or intestine protrudes through a weak place or defect within the abdominal muscle wall or groin of a patient. This condition commonly occurs in humans, particularly males. Hernias may result from a congenital defect whereby the patient is born with this problem, or may be caused by straining or lifting heavy objects. Heavy lifting has been found to create a large amount of stress upon the abdominal wall, which can cause a rupture or tearing at a weak point of the abdominal muscle to create the defect or opening. In any Hernia case, a patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution for correcting a hernia condition is surgery. During a surgical procedure, the defect is accessed and carefully examined, either through an open incision or endoscopically through an access port such as a trocar. In either case, careful examination is required due to the network of vessels and nerves that exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the open defect, and attaching the mesh patch to the abdominal wall or inguinal floor using sutures or surgical fasteners. The mesh patch acts as a barrier and prevents expulsion of bowel through the defect.

Inguinal hernia repair involves the placement and fixation of a surgical mesh over a defect. There are specific sites that must be avoided due to the presence of blood vessels and nerves (known as the triangle of doom and triangle of pain), and specific sites that can be used for mesh fixation (Cooper's ligament, Lacunar ligament, abdominal wall). The Cooper's ligament, also known as the Pectineal ligament, lies on the superior pubic ramus of the pelvis. The thickness of this ligament is typically 1 mm to 3 mm.

Suture is the standard for hernia mesh fixation and is used for affixing mesh to the Cooper's ligament. Suturing of the mesh patch to the inguinal floor can be well suited to open procedures. In laparoscopic procedures, however, suturing is not preferred due to the greater skill and time required.

Adhesives have also been used for hernia mesh fixation, including fibrin and cyanoacrylate adhesives. The use of adhesives has been limited, however, due to high cost, special storage conditions, preparation, and diminished effectiveness on wet tissue.

Self-adhering surgical mesh is also used for laparoscopic hernia repair. Some surgeons have noted some difficulty in handling due to self-adhesion. In addition, surgeons often prefer the additional security of mechanical fixation of the mesh to tissue.

Surgical fasteners are often used during endoscopic or open procedures for attaching mesh patches to the inguinal floor. One of the earliest types of endoscopic procedures involves the use of a surgical stapler that dispenses staples into tissue. The surgical stapler typically has a stack of unformed staples that are contained within a stapling cartridge in a serial fashion. The staples are sequentially advanced or fed within an applicator instrument by a spring mechanism. As the staples are dispensed, an anvil engages the arms of the staple to bend the arms into a closed, clamping position.

Another hernia mesh attachment instrument uses a helical wire fastener that resembles a small section of spring. Multiple helical wire fasteners may be stored serially within a shaft of an applicator instrument, and may be corkscrewed or rotated into tissue. A load spring may be used to bias or feed the plurality of helical fasteners distally within the shaft.

Surgical fasteners have generally been made of metal, such as stainless steel, nitinol, or titanium. The use of metal fasteners was necessary to provide for sufficient holding strength, penetration of various prosthetic meshes, and for ease of manufacture. Although metallic mesh fixation devices are very effective at securing mesh to the Cooper's ligament, it is suspected that metallic devices contribute to long-term patient pain and discomfort.

In response to problems associated with using permanent, metal fasteners, absorbable mesh fixation devices have been developed for securing mesh to tissue. Until recently, there were no absorbable tissue fasteners available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, there remains a need for absorbable tissue fasteners for affixing mesh to tissue that can be applied laparoscopically, whereby the tissue fastener has a minimum profile.

Thus, in spite of the above advances, there remains a need for further improvements in surgical fasteners. In particular, there remains a need for surgical fasteners having a minimum profile, surgical fasteners having shorter anchoring legs that achieve sufficient anchoring force in tissue, surgical fasteners that may be applied laparoscopically, surgical fasteners that have superior holding strength, surgical fasteners that will not injure vessels and nerves, and surgical fasteners that are absorbable.

SUMMARY OF THE INVENTION

In one embodiment, a surgical fastener is used for anchoring medical devices, such as surgical mesh, to tissue. The surgical fastener is preferably absorbable. In one embodiment, the surgical fastener preferably includes first and second legs lying in a first plane, and third and fourth legs lying in a second plane that is orthogonal with the first plane. The surgical fastener desirably has a bridge interconnecting proximal ends of the legs for forming a closed end of the surgical fastener. In one embodiment, each leg preferably has a proximal end, a distal end, and an insertion tip with a distal point located at the distal end of the leg. Each leg desirably has an insertion tool alignment guide formed therein that extends between the proximal and distal ends of the leg and along a longitudinal axis that is aligned with the distal point of the insertion tip.

In one embodiment of the present invention, the distal points on the insertion tips may have facets. In other embodiment, however, the distal points on the insertion tips may have smooth surfaces such as conical shaped distal points.

In one embodiment, each leg of the surgical fastener has a tissue engaging barb projecting toward the proximal end of the leg and outwardly away from the leg. In one embodiment, the tissue engaging barb desirably projects proximally from a proximal end of the insertion tip at the distal end of the leg.

In one embodiment, each insertion tip preferably has a proximal end having an insertion tool seating surface that faces toward the proximal end of the leg associated therewith. The insertion tool seating surface is preferably aligned with both the insertion tool alignment guide and the distal point of the insertion tip. In one embodiment, the insertion tool seating surface defines a distal-most end of the insertion tool alignment guide. The insertion tip preferably extends along an axis that is coaxial with the longitudinal axis of the insertion tool alignment guide. The longitudinal axis of the insertion tool alignment guide desirably intersects the distal point of the insertion tip.

In one embodiment, a surgical fastener for anchoring medical devices to tissue desirably has three legs including first and second legs and a third leg located between the first and second legs. In one embodiment, the first and second legs are outer legs and the third lag is a centrally located leg that is in between the first and second, outer legs. The three legs preferably lie in a single plane.

In one embodiment, a bridge interconnects the proximal ends of the three legs for forming a closed end of the surgical fastener. Each leg preferably has a proximal end, a distal end, an insertion tip with a distal point located at the distal end of the leg, and an insertion tool alignment guide that extends between the proximal and distal ends of the leg and along a longitudinal axis that is aligned with the distal point of the insertion tip.

In one embodiment, the first leg preferably has insertion tool alignment guide formed thereon that extends between the proximal and distal ends of the first leg and along a first longitudinal axis that is aligned with the distal point of the insertion tip of the first leg. The second leg preferably has an insertion tool alignment guide that extends between the proximal and distal ends of the second leg and along a second longitudinal axis that is aligned with the distal point of the insertion tip of the second leg. The third leg desirably has an insertion tool alignment guide that is accessible at a proximal end of the bridge and that extends between the proximal and distal ends of the third leg and along a third longitudinal axis that is aligned with the distal point of the insertion tip of the third leg.

In one embodiment, the first, second and third longitudinal axes of the three respective insertion tool alignment guides are parallel to one another.

In one embodiment, each leg preferably has at least one tissue engaging barb projecting toward the proximal end of the leg and outwardly away from the leg. The tissue engaging barbs desirably project proximally from a proximal end of an insertion tip.

In one embodiment, each insertion tip preferably has an insertion tool seating surface that defines a distal-most end of the insertion tool alignment guide. Each insertion tip desirably extends along an axis that is coaxial with the longitudinal axis of the insertion tool alignment guide associated therewith. The longitudinal axis of each insertion tool alignment guide preferably intersects the distal point of the insertion tip associated therewith.

In one embodiment, the insertion tool alignment guides on the first and second legs preferably include grooves formed in outer surfaces of the first and second legs, and the insertion tool alignment guide on the third leg comprises a blind bore formed in the third leg.

In one embodiment, the first leg has a first barb projecting toward the proximal end of the first leg, and the second leg has a second barb projecting toward the proximal end of the second leg, whereby the first and second barbs on the respective first and second legs project outwardly away from one another.

In one embodiment, the bridge interconnecting the proximal ends of the three legs preferably defines a proximal end insertion tool seating surface.

In one embodiment, a surgical fastener for anchoring a medical device, such as a mesh, to tissue preferably includes a base having an outer perimeter, a proximal surface, and a distal surface, and a plurality of legs projecting from the distal surface of the base. The legs are preferably evenly spaced from one another adjacent the outer perimeter of the base. In one embodiment, each leg preferably has a proximal end secured to the distal surface of the base and a distal, free end with a pointed tip and at least one tissue-engaging barb projecting therefrom.

In one embodiment, the pointed insertion tips of the surgical fasteners are cut or have defined chisel points, which enable the insertion tips to cut during insertion, thereby improving the ability of the surgical fasteners to penetrate difficult materials such as GORE® dual mesh. Insertion tips having compound cut or chiseled angles may also be used to allow for stronger, yet shorter tip designs.

In one embodiment, surgical fasteners may have conical-shaped insertion tips that create a puncture rather than a cut, thereby improving holding force. Although the present invention is not limited by any particular theory of operation, it is believed that conical-shaped insertion tips create only a single point of stress concentration, whereby the section of the surgical fastener that follows must expand the hole radially. It is believed that this may make it harder for the rest of the surgical fastener to make it through the hole, but may potentially increase retention forces by making a tighter hole.

In one embodiment, surgical fasteners may incorporate active agents such anti-microbials and anti-adhesion materials. In one embodiment, surgical fasteners may incorporate radio-opacity to enable the surgical fasteners to be visible on x-ray imaging machines.

In one embodiment, ribs are formed on the outside of each leg of the surgical fastener, and an insertion fork has a mating channel that straddles each of the ribs. The ends of each fork tine bottom out in recesses or seating surfaces formed in the insertion tips of the surgical fastener. This above design transfers the complexity of manufacturing recesses from the legs of the surgical fastener to the tines of the insertion tool. This feature is especially important because the applicator instrument will preferably dispense multiple surgical fasteners (as opposed to just one insertion fork).

In one embodiment, an insertion tool includes a bridge that extends between proximal ends of fork tines. The shape of the bridge on the insertion tool may substantially conform to the proximal face of the bridge at the proximal end of the surgical fastener. In one embodiment, the insertion fork is designed so that the bridge element of the insertion fork comes into contact with the proximal end of the surgical fasteners at the time, or just prior to when, the distal ends of each fork bottoms out or engages the seating surfaces formed in the insertion tips of the surgical fastener. In one embodiment, the bridge of the insertion fork may include a softer (with respect to the durometer of the rest of the insertion fork) elastomeric material to reduce the required dimensional precision necessary to assure contact of the bridge and distal fork ends with the surgical fastener at about the same time. This configuration preferably enables the driving force behind the surgical fastener to be distributed along a greater surface area of the surgical fastener so as to reduce the pressure generated between the insertion tool and the surgical fastener.

These and other preferred embodiments of the invention will be described in more detail below.

BRIEF DESCRIPTION OF THE DRAWINGS

FIG. 3E shows a proximal end view of the surgical fastener shown in FIG. 3A.

FIG. 3F shows a distal end view of the surgical fastener shown in FIG. 3A.

FIG. 4 shows a method of securing a medical device to tissue using the surgical fastener shown in FIGS. 3A-3F, in accordance with another embodiment of the present invention.

FIG. 6 shows a method of securing a medical device to tissue using the surgical fastener shown in FIGS. 5A-5E, in accordance with one embodiment of the present invention.

DETAILED DESCRIPTION

Figure 1A:
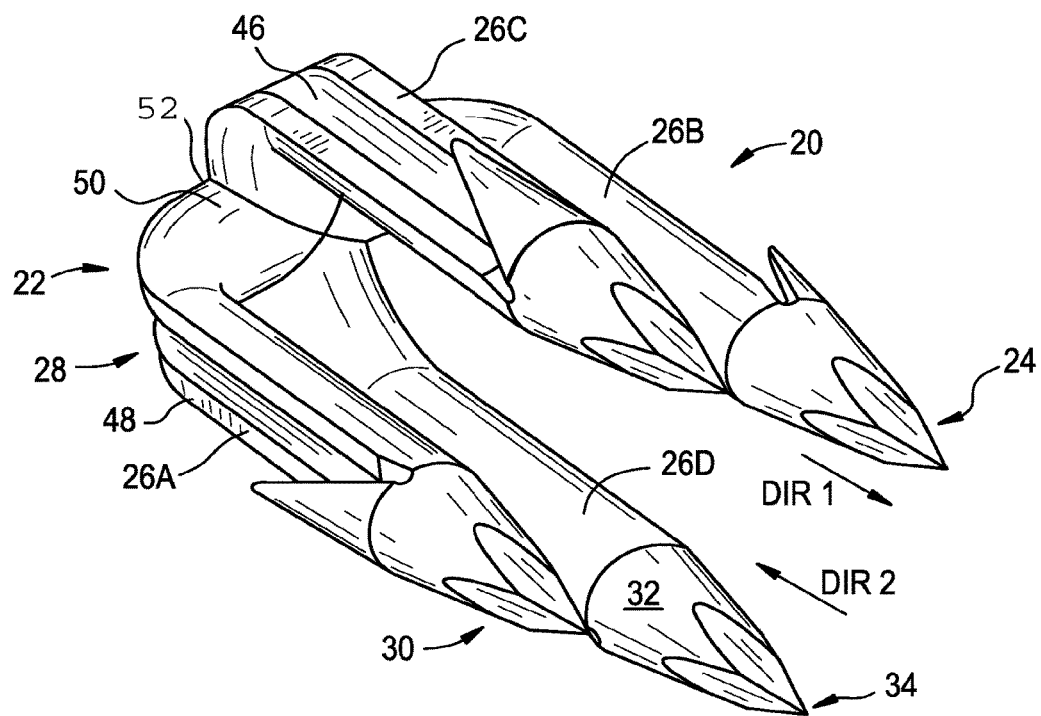
FIG. 1A shows a perspective view of a surgical fastener, in accordance with one embodiment of the present invention.
Figure 1B:
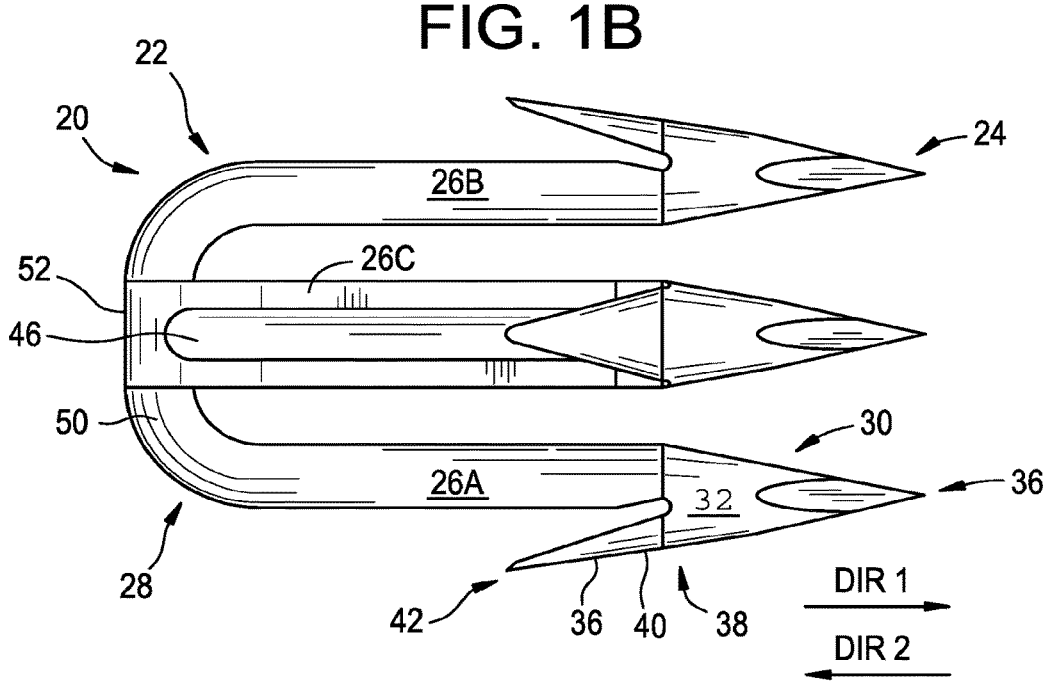
FIG. 1B shows a side view of the surgical fastener shown in FIG. 1A.

Referring to FIGS. 1A and 1B, in one embodiment, a surgical fastener 20 for securing a medical device such as surgical mesh to tissue preferably includes a proximal end 22 and a distal end 24. The surgical fastener 20 is preferably absorbable. In one embodiment, the surgical fastener 20 preferably has four legs including first and second legs 26A, 26B that lie in a first plane and third and fourth legs 26C, 26D that lie in a second plane that is orthogonal to the first plane. In one embodiment, the first and second planes define an angle relative to one another. In one embodiment, the angle is about 90 degrees.

In one embodiment, each of the four legs 26A-26D has the same length, dimensions and structure. In one embodiment, each leg 26A-26D preferably has a proximal end 28 adjacent the proximal end 22 of the surgical fastener 20, and a distal end 30 adjacent the distal end 24 of the surgical fastener 20. The distal end 30 of each leg 26A-26D desirably includes an insertion tip 32 having a distal point 34 adapted to pierce mesh and/or tissue during insertion of the surgical fastener into tissue. In one embodiment of the present invention, the distal points have facets. In other embodiment, however, the distal points may have smooth surfaces such as conical shaped distal points.

In one embodiment, each leg 26A-26D preferably includes a tissue anchoring element. In one embodiment, the tissue anchoring element may be a tissue engaging barb 36 that projects proximally and outwardly from a proximal end 38 of the insertion tip 32. The tissue engaging barb 36 preferably has a base 40 that is secured to the proximal end 38 of the insertion tip 32 and a proximal tip 42 that is spaced away from the leg 26A-26D. In one embodiment, the tissue engaging barb 36 has a notch 44 formed therein that enables the barb 36 to flex relative to the insertion tip 32 and the leg 26A. The tissue engaging barb 36 is desirably flexible so that the proximal tip 42 is cable of flexing/moving toward and away from the respective leg 26A-26D associated with the barb. In one embodiment, the barb 36 flexes inwardly toward the leg 26A when the distal end 24 of the surgical fastener 20 is advanced into tissue in the direction designated DIR 1. In one embodiment, the barb 36 flexes away from the leg 26A when the surgical fastener 20 is pulled in the opposite direction designated DIR 2 for anchoring the surgical fastener in the tissue and/or resisting extraction of the surgical fastener 20 from tissue.

In one embodiment, each leg 26A-26D preferably has an insertion tool alignment guide 46 provided thereon for enabling an insertion tool to engage the surgical fastener 20 and advance/drive the distal end 24 of the surgical fastener into tissue in the direction designated DIR 1. The insertion tool alignment guide 46 preferably extends between the proximal end 28 and the distal end 30 of each leg 26 and terminates at an insertion tool seating surface (not shown) provided on the insertion tip 32 associated with the leg. The insertion tool, alignment guide may be any structure that enables an insertion tool to secure the surgical fastener and, while maintaining control of the orientation of the surgical fastener, drive the surgical fastener into tissue. In one embodiment, the insertion tool alignment guide 46 is preferably a groove that is formed in the outer surface 48 of the leg 26. In one embodiment, the alignment guide may be a rail or projection provided on the leg. In one embodiment, the insertion tool alignment guides 46 that are provided on the first and second legs 26A, 26B face away from one another, and the insertion tool alignment guides that are provided on the third and fourth legs 26C, 26D face away from one another. In one embodiment, the barbs 36 on the first and second legs project away from one another, and the barbs on the third and fourth legs project away from one another.

Referring to FIGS. 1A and 1B, in one embodiment, the surgical fastener 20 preferably includes a bridge 50 that interconnects the proximal ends 28 of the four legs 26A-26D. The bridge forms a closed end of the surgical fastener. The bridge desirably has a proximal surface 52 that extends along the proximal end 22 of the surgical fastener 20. The proximal surface 52 provides an additional surface that may be engaged by an insertion tool for driving the surgical fastener 20 into tissue in the direction designated DIR 1.

Figure 1C:
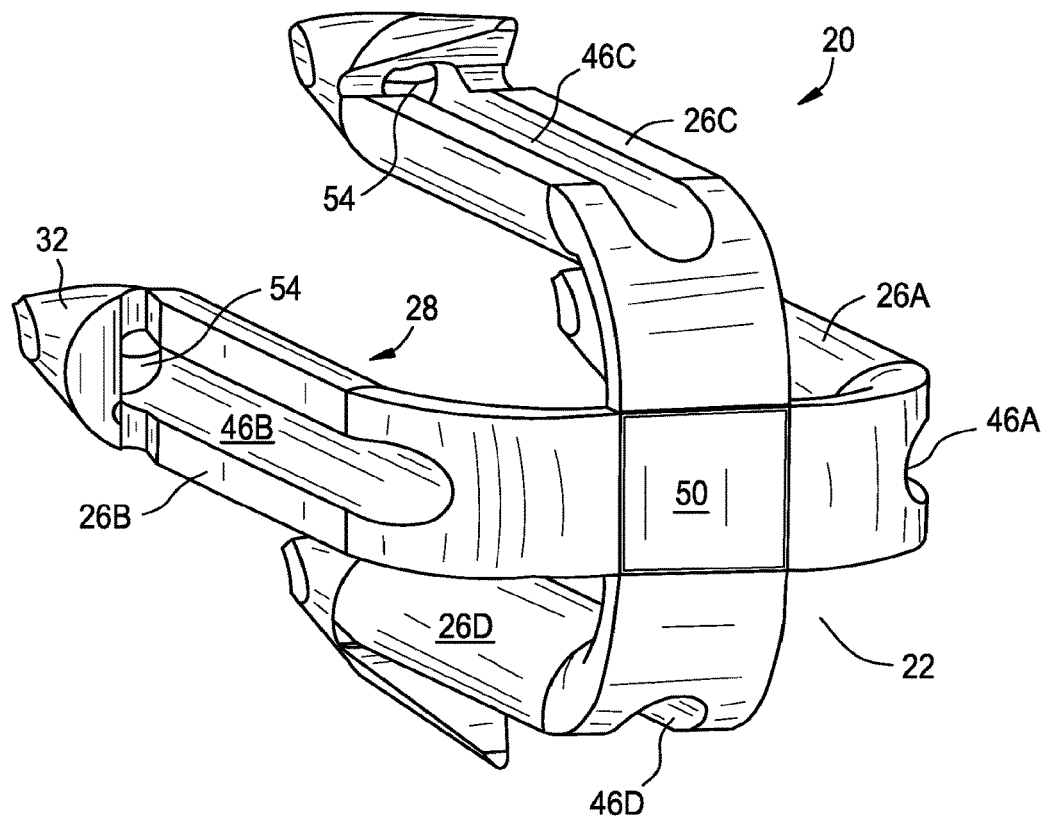
FIG. 1C shows a perspective view of a proximal end of the surgical fastener shown in FIG. 1A.

Referring to FIG. 1C, in one embodiment, each leg 26A-26D preferably has a respective insertion tool alignment guide 46A-46D formed therein. In one embodiment, the insertion tool alignment guide provided on each leg desirably has the same length, dimensions and structure. The insertion tool alignment guides 46A-46D preferably extend from the proximal ends 28 of each leg 26 to an insertion tool seating surface 54 provided on the insertion tip 32 of each leg. The proximal ends of the insertion tool alignment guides 46A-46D are preferably accessible at the proximal end 22 of the surgical fastener 20 so that an insertion tool having tines (FIG. 2) may be advanced into the insertion tool alignment guides. The proximal ends 28 of the respective legs 26 are interconnected by the bridge 50 at the proximal end of the surgical fastener 20.

Figure 1D:
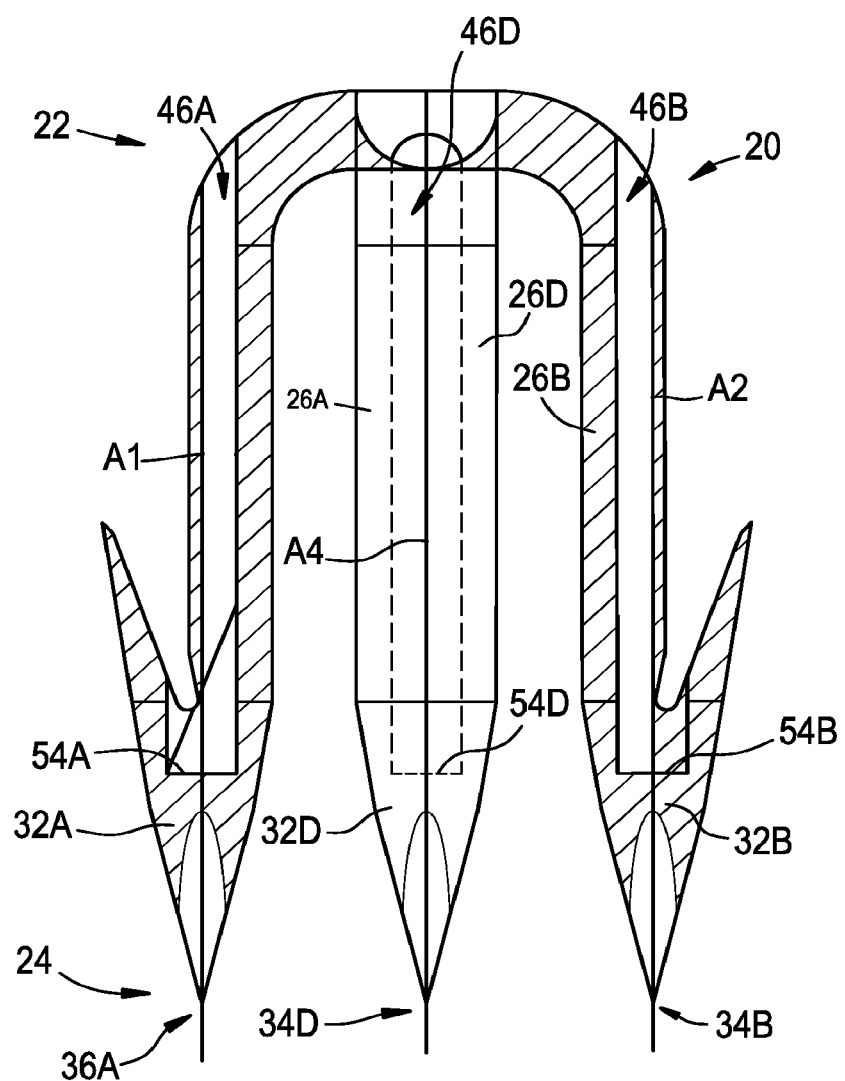
FIG. 1D shows a cross-sectional view of the surgical fastener shown in FIG. 1B.

Referring to FIG. 1D, in one embodiment, the insertion tool alignment guides 46 preferably extend along the lengths of the respective legs 26. In FIG. 1D, the first leg 26A has a first insertion tool alignment guide 46A that extends along a first longitudinal axis A1, which is aligned with the first distal point 34A on the first insertion tip 32A. The first longitudinal axis A1 preferably passes through the first distal point 34A. The distal end of the first insertion tool alignment guide 46A desirably terminates at a first insertion tool seating surface 54A provided on the first insertion tip 32A. The second leg 26B has a second insertion tool alignment guide 46B that extends along a second longitudinal axis A2, which is aligned with the second distal point 34B on the second insertion tip 32B. The second longitudinal axis A2 preferably passes through the second distal point 34B. The distal end of the second insertion tool alignment guide 46B terminates at a second insertion tool seating surface 54B provided on the second insertion tip 32B. The fourth leg 26D has an insertion tool alignment guide 46D that extends along a fourth longitudinal axis A4, which is aligned with the fourth distal point 34D on the fourth insertion tip 32D. The fourth longitudinal axis A4 preferably passes through the fourth distal point 34D. The distal end of the fourth insertion tool alignment guide 46D terminates at a fourth insertion tool seating surface 54D provided on the fourth insertion tip 32D. Although not shown in FIG. 1D, the third leg 26C (FIG. 1C) has an insertion tool alignment guide 46C and an insertion tool seating surface 54C with similar structure as shown for the first leg 26A, the second leg 26B, and the fourth leg 26D. The insertion tool alignment guide for the third leg preferably extends along a third longitudinal axis that passes through the third distal point of the third insertion tip.

Figure 1E:
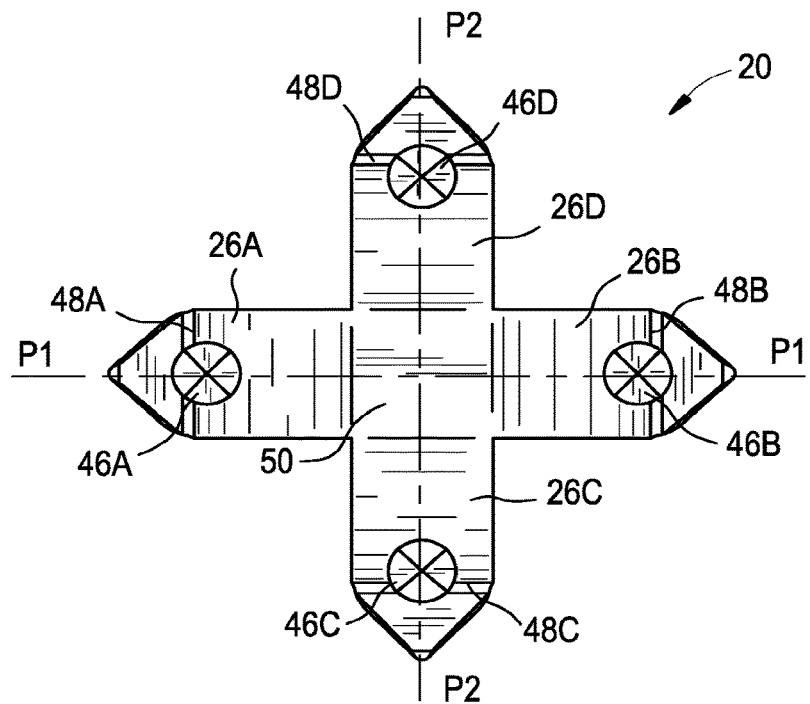
FIG. 1E shows a proximal end view of the surgical fastener shown in FIG. 1A.

Referring to FIG. 1E, the bridge 50 preferably interconnects the proximal ends of the four legs 26A-26D of the surgical fastener 20. Each leg 26A-26D desirably has an insertion tool alignment guide 46A-46D formed therein that extends between the proximal ends of the legs and the insertion tips at the distal ends of the legs. In one embodiment, the insertion tool alignment guides 46A-46D are grooves formed in the outer faces 48A-48D of the respective legs 26A-26D. The insertion tool alignment guides desirably extend along respective longitudinal axes A1-A4, which are parallel to one another. In one embodiment, an insertion tool having four tines is utilized for driving the surgical fastener 20 into tissue. The spacing, pattern, lengths and dimensions of the tines preferably matches the spacing and pattern of the insertion tool alignment guides 48A-48D formed in the respective legs 26A-26D. When the insertion tool is advanced into the insertion tool alignment guides, the distal-most ends of the tines preferably abut against the insertion tool seating surfaces provided at the distal ends of the respective insertion tool alignment guides.

Figure 1F:
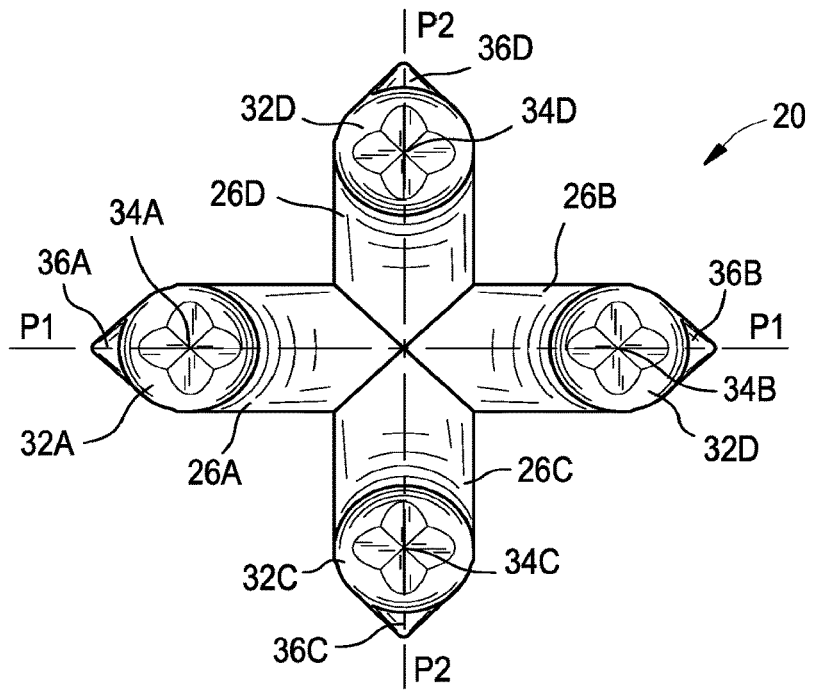
FIG. 1F shows a distal end view of the surgical fastener shown in FIG. 1A.

Referring to FIG. 1F, the distal ends of the four legs 26A-26D terminate at respective insertion tips 32A-32D, each insertion tip having a distal point 34A-34D. In one embodiment, a single tissue engaging barb 36A-36D projects from the proximal end of each insertion tip. Other embodiments may have two or more barbs extending from the proximal ends of the insertion tips. The barbs 36A, 36B on the first and second legs 26A, 26B project away from one another, and the barbs 36C, 36D on the third and fourth legs 26C, 26D project away from one another.

Referring to FIGS. 1E and 1F, the first and second legs 26A, 26B preferably lie in a first plane P1, and the third and fourth legs 26C, 26D preferably lie in a second plane P2. In one embodiment, the first plane P2 is orthogonal to the second plane P2. In one embodiment, the first and second planes P1, P2 define an angle, which may be about 90 degrees.

Although the present invention is not limited by any particular theory of operation, it is believed that providing a surgical fastener with more than two legs enables shorter legs to be used while still attaining sufficient anchoring strength for insuring that the fasteners may not be readily extracted from tissue. The shorter legs are able to penetrate surgical mesh and affix to this soft tissue anatomical structures, such as a Cooper's ligament or fascia that cover bone. The barbs at the distal ends of the legs provide additional anchoring force. Moreover, the insertion tool alignment guides provide for enhanced control over the orientation of the legs of the surgical fasteners as the distal ends of the legs are driven into tissue.

Figure 2:
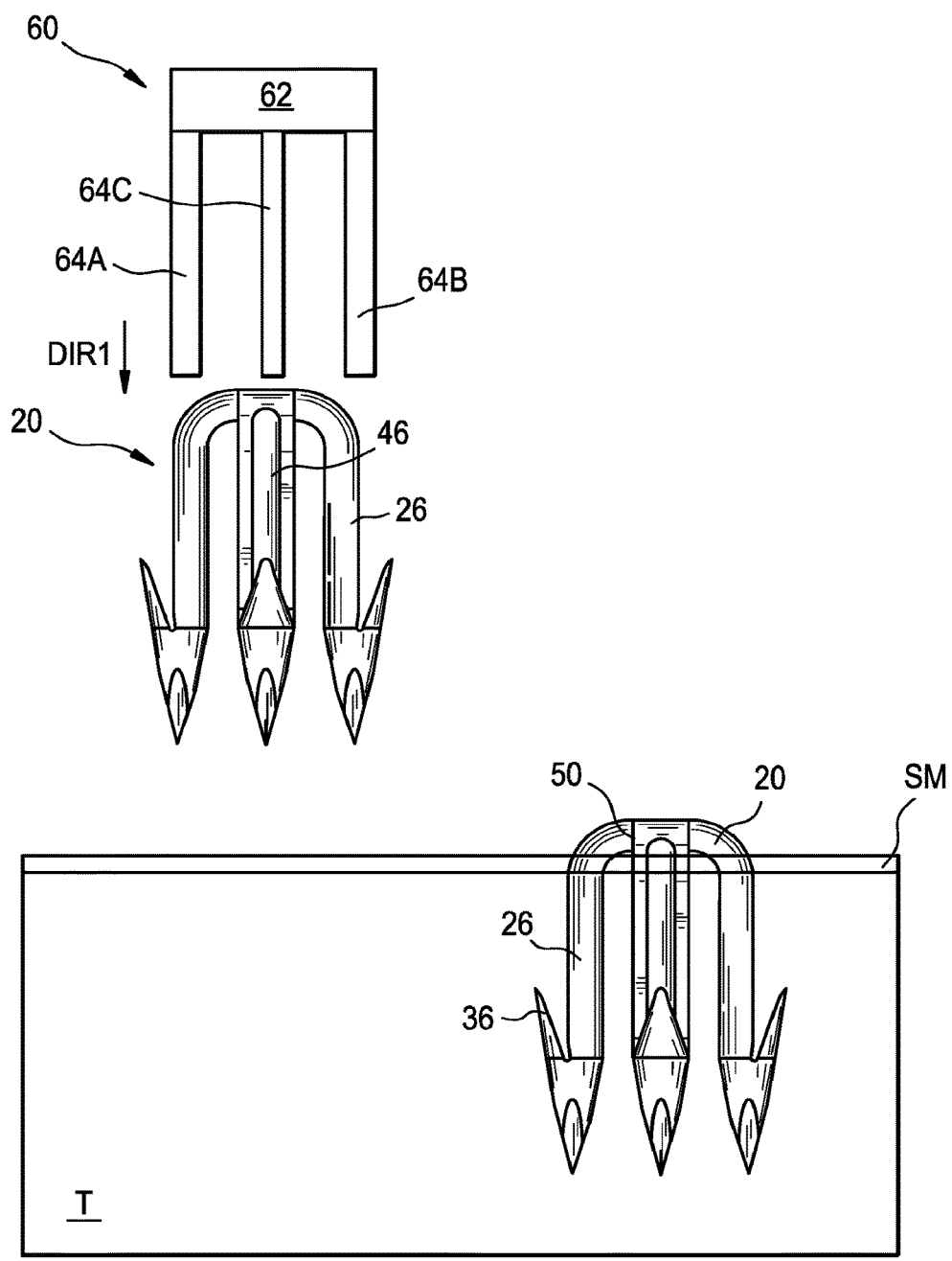
FIG. 2 shows a method of securing a medical device to tissue using the surgical fastener shown in FIGS. 1A-1F, in accordance with one embodiment of the present invention.

Referring to FIG. 2, in one embodiment, an insertion tool 60 is utilized for advancing the surgical fastener 20 into tissue. In one embodiment, the insertion tool 60 has a base 62 and insertion tines 64 projecting from a distal face 66 of the base 62. Although only three tines 64A, 64B, and 64C are shown in FIG. 2, the insertion tool 60 preferably has four tines or one tine for each leg 26 of the surgical fastener 20.

In one embodiment, the distal ends of the respective tines 64 slide into the insertion tool alignment guides 46 until the distal ends of the tines engage the insertion tool seating surfaces 54 (FIG. 1D). In one embodiment, as the distal ends of the tines engage the insertion tool seating surfaces, the distal face 66 of the base 62 simultaneously engages the proximal end of the surgical fastener for transferring additional insertion force to the surgical fastener. The insertion tool is preferably advanced in the direction designated DIR 1 for driving the surgical fastener 20 through a surgical mesh SM and into tissue T for securing the surgical mesh in place on the tissue. The tissue engaging barbs 36 at the distal ends of the legs 26 anchor the surgical fastener in place in the tissue. A plurality of surgical fasteners may be passed through the surgical mesh SM for securing the mesh to the tissue.

The cruciform shaped pattern of the legs 26 preferably capture mesh between the legs and the bridge 50. By using four legs rather than two legs found in prior art devices, the legs may be made shorter for use in thinner tissue, while still generating sufficient anchoring force so that the surgical fastener may not be readily extracted from the tissue T.

In one embodiment, the legs 26 of the surgical fastener have a length that enables the surgical fastener to effectively secure a prosthetic device in place with the legs fully engaged with Cooper's ligament. In one embodiment, the legs 26 have a length of about 1-4 mm and more preferably about 2-3 mm. In one embodiment, the insertion tool alignment guides 46 and the tines 64 on the insertion tool have respective lengths that accommodate the above-described lengths of the legs 26.

Figure 3A:
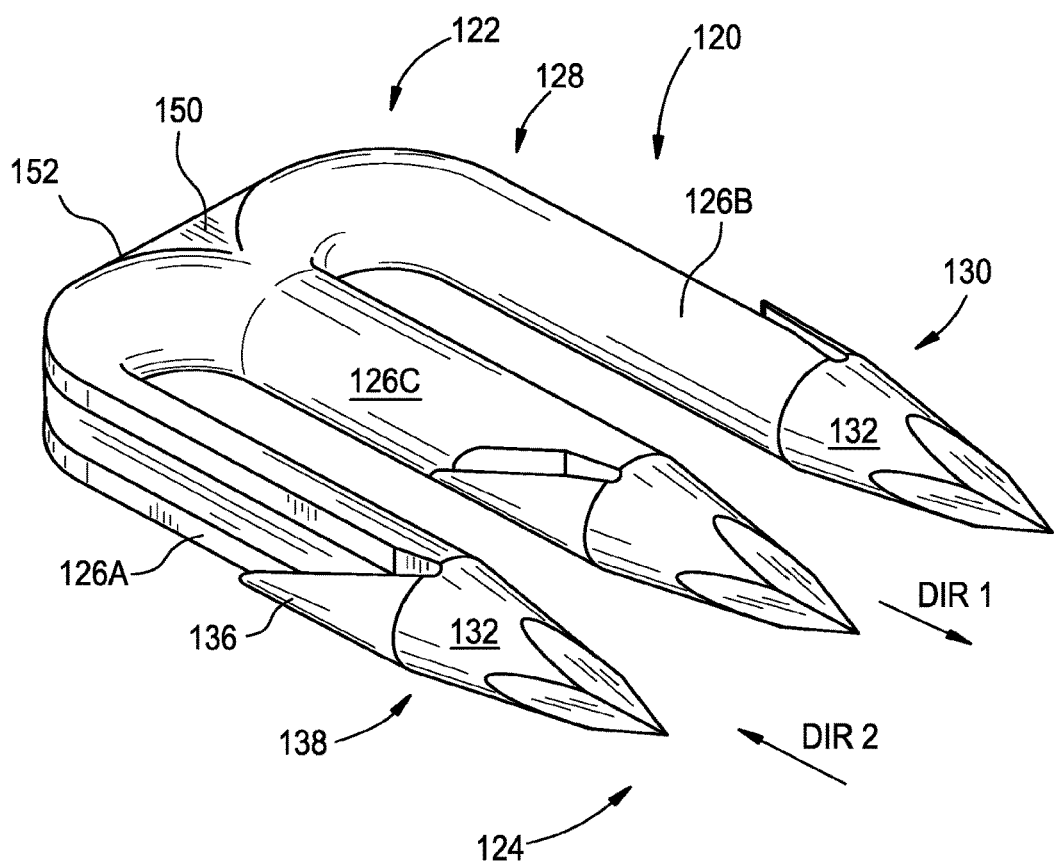
FIG. 3A shows a perspective view of a distal end of a surgical fastener, in accordance with another embodiment of the present invention.
Figure 3B:
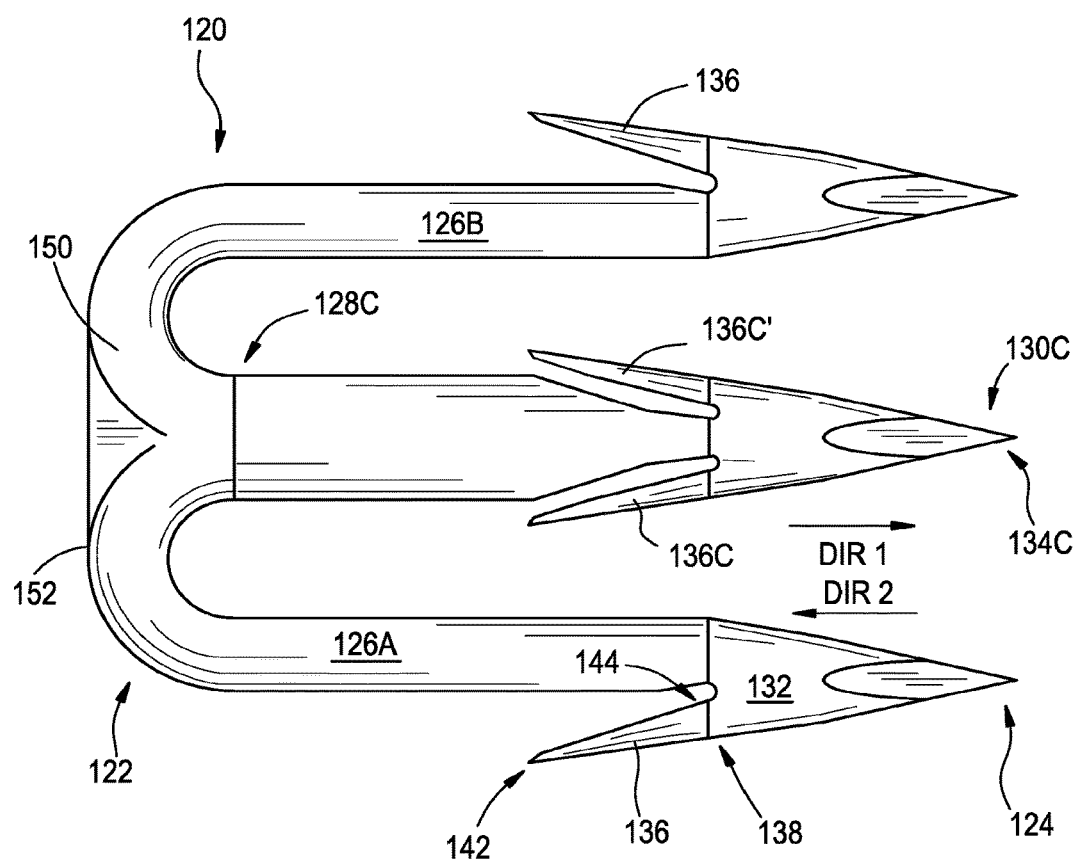
FIG. 3B shows a side view of the surgical fastener shown in FIG. 3A.

Referring to FIGS. 3A and 3B, in one embodiment, a surgical fastener 120 for securing a prosthetic device such as a surgical mesh to tissue preferably includes a proximal end 122 and a distal end 124. The surgical fastener 20 preferably includes three legs 126A, 126B, and 126C lying in a single plane. The first and second legs 126A and 126B are outer legs and the third leg 126C is a centrally located leg that is positioned between the two outer legs 126A, 126B.

In one embodiment, each leg 126 preferably has a proximal end 128 adjacent the proximal end 122 of the surgical fastener 120, and a distal end 130 adjacent the distal end of the surgical fastener 120. The distal end 130 of each leg 126 desirably includes an insertion tip 132 having a distal point 134 adapted to pierce a surgical mesh and tissue during insertion of the surgical fastener 120 into tissue. In one embodiment of the present invention, the distal points have facets. In other embodiment, however, the distal points may have smooth surfaces such as conical shaped distal points.

The surgical fastener 120 preferably includes a bridge 150 that interconnects the proximal ends of the three legs 126A-126C. The bridge 150 has a proximal face 152 that defines a seating surface for an insertion tool for driving the surgical fastener 120 into tissue.

In one embodiment, the first and second outer legs 126A, 126B each have a tissue anchoring element such as a tissue engaging barb 136 that projects proximally from a proximal end 138 of the insertion tip 132. The tissue engaging barb 136 preferably has a base 140 that is secured to the proximal end 138 of the insertion tip 132 and a proximal tip 142 that is spaced away from the leg 126. In one embodiment, the tissue engaging barb 136 has a notch 144 formed therein that enables the barb 136 to flex relative to the insertion tip 132 and the leg 126. The tissue engaging barb 136 is desirably flexible so that the proximal tip 142 is cable of moving toward and away from the leg 126. In one embodiment, the barb 136 flexes inwardly toward the leg 126 when the distal end 124 of the surgical fastener 120 is advanced into tissue in the direction designated DIR 1. In one embodiment, the barb 136 flexes away from the leg 126 when the surgical fastener 120 moves in the direction designated DIR 2 for preventing extraction of the surgical fastener. The barbs preferably anchor the surgical fastener in tissue to prevent the surgical fastener from being extracted from the tissue.

Referring to FIG. 3B, the central leg 126C has a proximal end 128C, and a distal end 130C having an insertion tip 132C with a distal point 134C. The central leg 126C has a pair of tissue engaging barbs 136C, 136C' that project proximally from a proximal end of the insertion tip 132C. The pair of barbs 136C, 136C' are designed to flex as described above to facilitate anchoring the surgical fastener 120 in tissue.

Figure 3C:
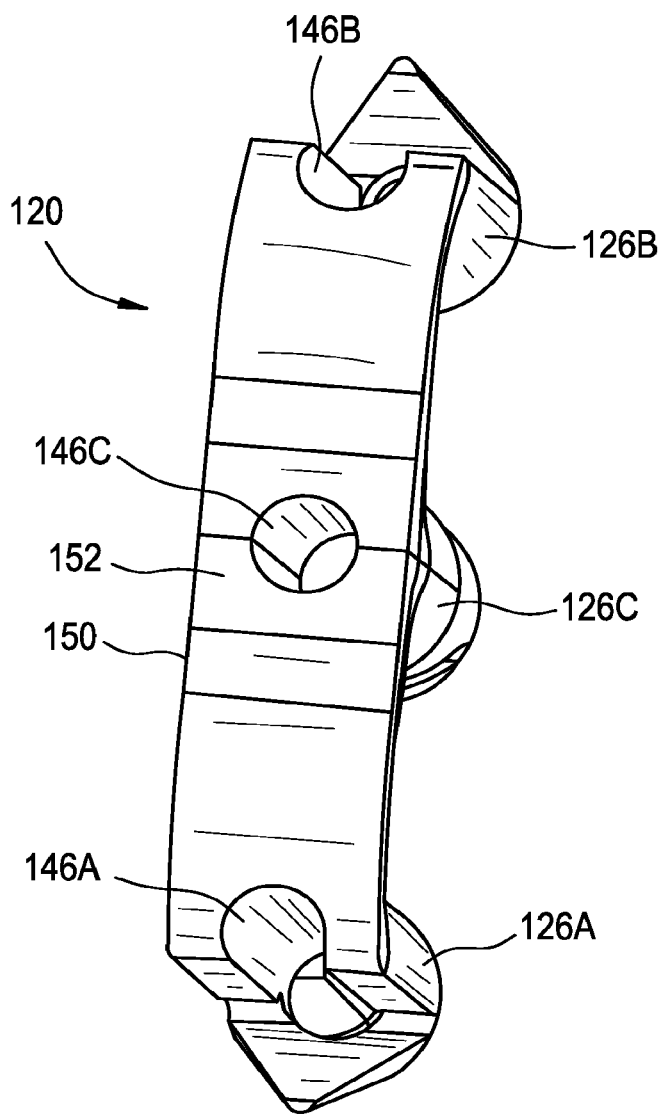
FIG. 3C shows a perspective view of a proximal end of the surgical fastener shown in FIG. 3A.

Referring to FIG. 3C, in one embodiment, the first leg 126A of the surgical fastener 120 has a first insertion tool alignment guide 146A provided thereon, the second leg 126B has a second insertion tool alignment guide 146B provided thereon, and the third or central leg 126C has a third insertion tool alignment guide 146C provided thereon. The insertion tool alignment guides may be elongated grooves or openings formed in the respective legs 126 of the surgical fastener 120. The insertion tool alignment guides 146A-146C are adapted to receive the tines of an insertion tool for driving a surgical fastener 120 into tissue. The insertion tool alignment guide 146C provided on the central leg 126C includes an opening accessible at the proximal face 152 of the bridge 150.

Figure 3D:
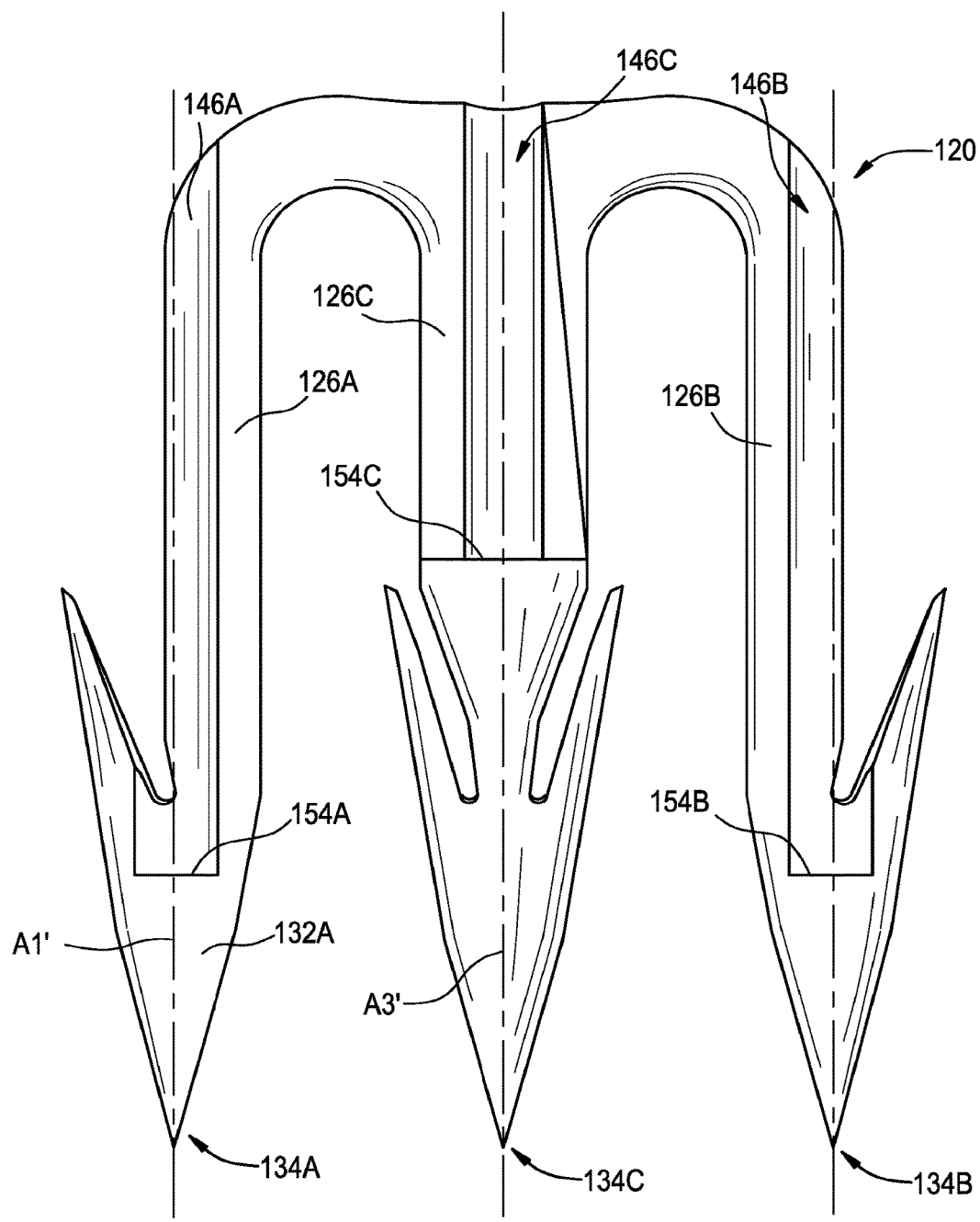
FIG. 3D shows a cross-sectional view of the surgical fastener shown in FIG. 3B.

Referring to FIG. 3D, in one embodiment, the insertion tool alignment guides preferably extend along the lengths of the respective legs 126A-126O. In FIG. 3D, the first leg 126A has a first insertion tool alignment guide 146A that extends along a longitudinal axis A1', which is aligned with the first distal point 134A on the first insertion tip 132A. The longitudinal axis A1' preferably passes through the first distal point 134A. The distal end of the first insertion tool alignment guide 146A terminates at a first insertion tool seating surface 154A provided on the first insertion tip 132A. The second leg 126B has an insertion tool alignment guide 146B that extends along a longitudinal axis A2', which is aligned with the second distal point 134B on the second insertion tip 132B. The second longitudinal axis A2' preferably passes through the second distal point 134B. The distal end of the second insertion tool alignment guide 146B terminates at a second insertion tool seating surface 154B provided on the second insertion tip 132B. The third leg 126C has an insertion tool alignment guide 146C that extends along a third longitudinal axis A3', which is aligned with the third distal point 134C on the third insertion tip 132C. The third longitudinal axis A3' preferably passes through the third distal point 134C. The distal end of the third insertion tool alignment guide 146C terminates at an insertion tool seating surface 154C provided on the third insertion tip 132C. The insertion tool alignment guide 126C for the center leg 126C preferably has a length that is shorter than the length of the first and second insertion tool alignment guides 146A, 146B for the respective first and second legs 126A, 126B. In one embodiment, the longitudinal axes A1', A2', and A3' of the respective insertion tool alignment guides 146A-146C are preferably parallel to one another. The longitudinal axes are preferably aligned with and intersect the respective distal tips 134A, 134B, 134C.

Referring to FIG. 3E, the surgical fastener 120 preferably includes the bridge 150 that interconnects the proximal ends of the three legs 126A-1260 (FIG. 3A). Each leg has an insertion tool alignment guide 146A-1460 formed therein that extends from the proximal ends of the legs to the insertion tips at the distal ends of the legs. In one embodiment, the first and second insertion tool alignment guides 146A and 146B are grooves formed in the outer faces 148A, 148B of the respective first and second legs 126A, 126B (FIG. 3A). The central insertion tool alignment guide 146C is preferably an elongated opening that is formed in the central or third leg 126C (FIG. 3A) of the surgical fastener. The insertion tool alignment guides 146A-146C are accessible at the proximal face of the bridge 150 and desirably extend along respective longitudinal axes A1'-A3' that are parallel to one another. In one embodiment, an insertion tool having three tines is utilized for advancing a distal end of the surgical fastener 120 into tissue. The spacing and pattern of the tines preferably matches the spacing and pattern of the insertion tool alignment guides 146A-1460 formed in the respective legs. When the insertion tool is advanced into the insertion tool alignment guides, the distal ends of the tines preferably abut against the insertion tool seating surfaces 154A-1540 (FIG. 3D) located at the distal ends of the respective insertion tool alignment guides.

Referring to FIG. 3F, the distal ends of the three legs 126A-126C terminate at respective insertion tips 132A-132C, each insertion tip having a distal point 134A-134C. A single tissue engaging barb 136A, 136B projects from the proximal ends of the respective first and second insertion tips 132A, 132B, and a pair of barbs 136C, 136C' project from the third insertion tip 132C. Referring to FIGS. 3E and 3F, the three legs 126A-126C preferably lie in a single plane P1'. In one embodiment, the barbs on the central leg 126C may be rotated 90 degrees so that the barbs on the central leg project along an axis that is orthoganol to the plane P1'.

Referring to FIG. 4, in one embodiment, an insertion tool 160 is utilized for advancing the three-legged surgical fastener 120 into tissue T for securing surgical mesh SM to the tissue T. In one embodiment, the legs 126 of the surgical fastener have a length that enables the surgical fattener to effectively secure the surgical mesh SM to tissue with the legs fully engaged with Cooper's ligament. In one embodiment, the legs 126 have a length of about 1-4 mm and more preferably about 2-3 mm. In one embodiment, the insertion tool 160 has a base 162 and three insertion tines 164A-164C projecting from a distal face 166 of the base 162. The tines on the insertion tool have respective lengths that accommodate the above-described lengths of the legs 126 and the respective insertion tool alignment guides of the legs. The central tine 164C is preferably shorter than the first and second outer tines 164A, 164B so that the length of the central tine matches the length of the insertion tool alignment guide for the central leg 126C.

In one embodiment, the three tines 164A-1640 slide into the respective insertion tool alignment guides 146A-146C (FIG. 3D) until the distal ends of the tines engage the respective insertion tool seating surfaces 154A-154C on each leg 126A-126C (FIG. 3D). Simultaneously, the distal face 166 of the base 162 of the insertion tool 160 engages the proximal face of the bridge 150 for providing additional insertion force. The insertion tool 160 preferably drives the surgical fastener 120 through the surgical mesh SM and into the tissue T for securing the surgical mesh in place on the tissue. The tines preferably control the orientation of the legs 126 as the legs are driven into tissue T. The tissue engaging barbs 136 at the distal ends of the legs 126 anchor the surgical fastener 120 in place within the tissue. A plurality of surgical fasteners may be passed through the surgical mesh SM for securing the mesh to the tissue.

Figure 5A:
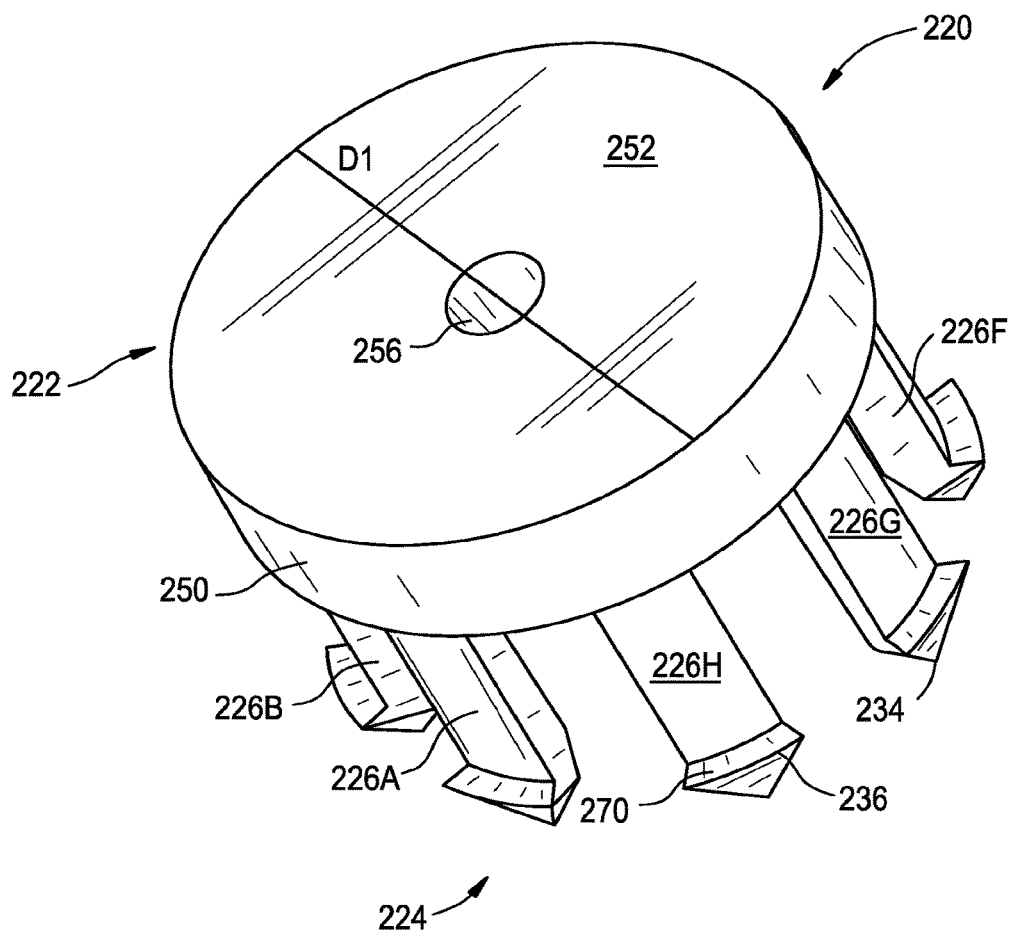
FIG. 5A shows a perspective view of a proximal end of a surgical fastener, in accordance with one embodiment of the present invention.
Figure 5B:
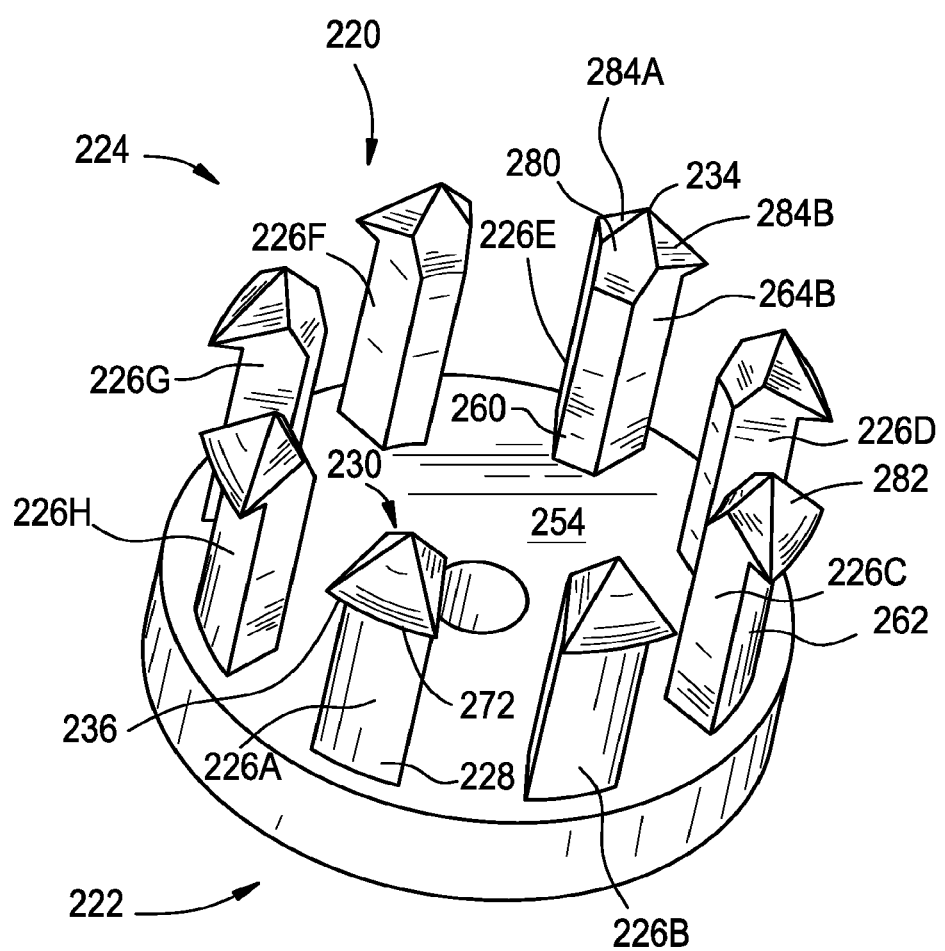
FIG. 5B shows a perspective view of a distal end of the surgical fastener shown in FIG. 5A.

Referring to FIGS. 5A and 5B, in one embodiment, a surgical fastener 220 for securing a medical device such as a surgical mesh to tissue preferably includes a proximal end 222 and a distal end 224. The surgical fastener 220 preferably includes a planar base 250 having a proximal face 252 and a distal face 254. The planar base 250 has a central opening 256 formed therein that extends from the proximal face 252 to the distal face 254. The central opening is desirably located at the center of the base 250. The base 250 desirably has an outer perimeter defining a diameter D1 of about 5 mm. The surgical fastener preferably has a plurality of legs 226A-226H that project from the distal face 254 of the planar base 250. The legs are preferably evenly spaced from one another around the perimeter of the base.

In one embodiment, each leg 226A-226H preferably has a proximal end 228 projecting from the distal face 254 of the base 250, and a distal, free end 230 adjacent the distal end 224 of the surgical fastener 220. The distal end 330 of each leg 326A-326H desirably includes a distal point 234 and a tissue anchor 236 that projects outwardly from the distal end of the leg 226. In one embodiment of the present invention, the distal points have facets. In other embodiment, however, the distal points may have smooth surfaces such as conical shaped distal points. After the distal ends of the legs have been driven into tissue, the tissue anchors 236 desirably retain the surgical fastener 220 in place within the tissue.

Figure 5C:
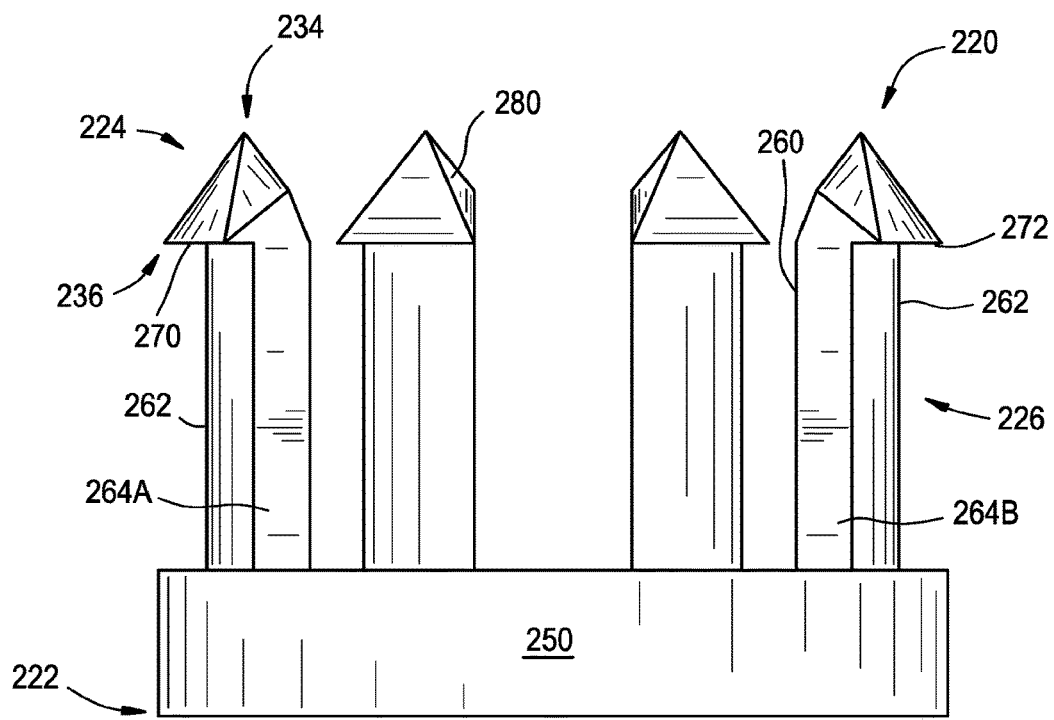
FIG. 5C shows a side view of the surgical fastener shown in FIG. 5A.

Referring to FIGS. 5B and 5C, in one embodiment, the surgical fastener 220 has eight legs 226A-226H that project from the distal face 254 of the base. The legs are desirably evenly spaced around the perimeter of the base 250. The legs are preferably positioned closer to the outer perimeter of the base than to the center of the base. In one embodiment, the legs are positioned adjacent, or slightly inward from the outer perimeter of the base. In one embodiment, each leg 226A-226H preferably has an inner face 260 that faces toward the center of the planar base 250, an outer face 262 that faces away from the center of the base, and a pair of side faces 264A, 264B that extend between the inner face 260 and the outer face 262 of the leg. In one embodiment, the inner face 260 defines a flat surface and the side faces 264A, 264B define flat surfaces that slope away from one another between the inner face 260 and the outer face 262 of the leg 226. In one embodiment, the outer faces 262 of the legs 226 define curved surfaces that mirror the curvature of the outer perimeter of the planar base 250.

In one embodiment, the distal end 224 of each leg 226 includes the distal point 234 and the tissue anchor 236. In one embodiment, the tissue anchor 236 includes a flat surface 270 that extends between the outer face 262 of the leg 226 and a curved surface 272 that defines the outermost edge of the tissue anchor 236.

Figure 5D:
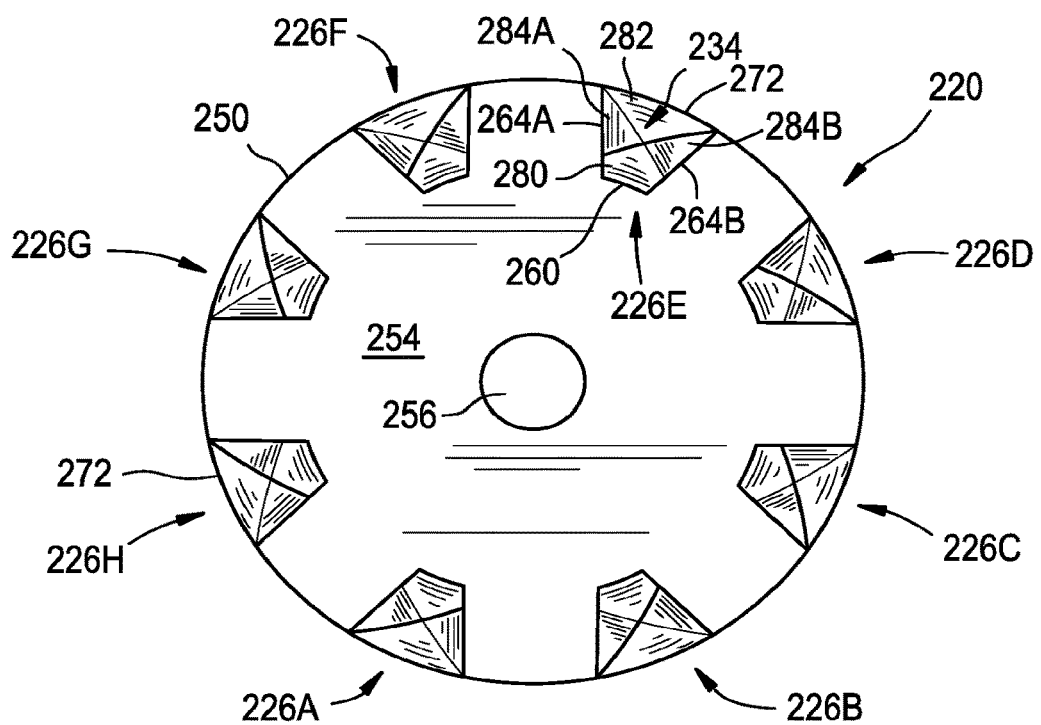
FIG. 5D shows a distal end view of the surgical fastener shown in FIG. 5A.

Referring to FIGS. 5C and 5D, in one embodiment, the distal end 224 of each leg 226 preferably includes an interior sloping surface 280 that slopes inwardly between the distal point 234 and the inner face 260 of the leg 226, an exterior sloping surface 282 that slopes outwardly between the distal point 234 and the curved edge 272 of the tissue anchor 236, and lateral sloping surfaces 284A, 284B that slope laterally between the distal point 234 and the pair of side faces 264A, 264B of the legs 226. Although the present invention is not limited by any particular theory of operation, it is believed that the interior sloping surface 260, the exterior sloping surface 282, and the pair of lateral sloping surfaces 284A, 284B enable the distal ends of the legs to move away from an object that may be encountered (e.g., bone) as the distal ends of the legs are driven into tissue.

Figure 5E:
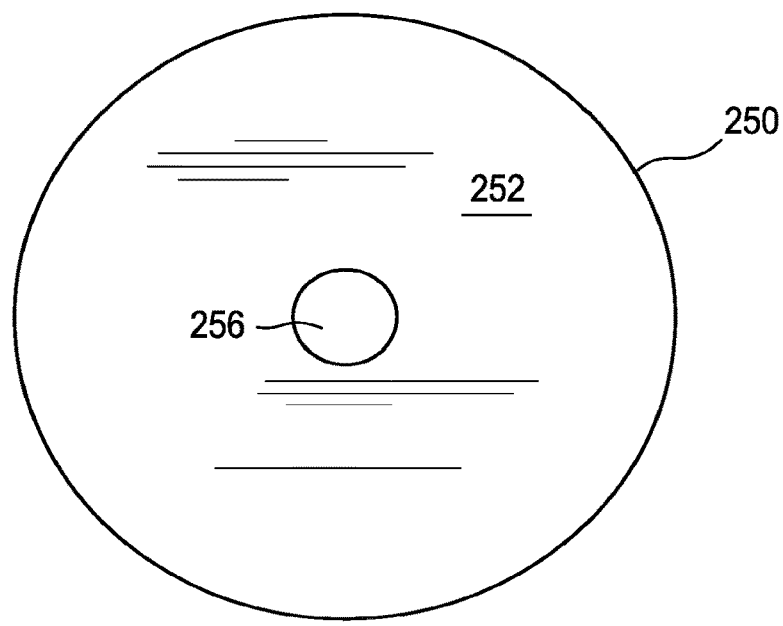
FIG. 5E shows a proximal end view of the surgical fastener shown in FIG. 5A.

Referring to FIG. 5D, the curved surface 272 at the outer perimeter of the tissue anchor 236 (FIG. 5A) is preferably aligned with and has the same curvature as the outer perimeter of the base 250. Referring to FIG. 5E, the central opening 256 is desirably accessible at the proximal face 252 of the base 250. As will be described in more detail herein, the central opening is adapted to receive at least one tine of an insertion tool for controlling the orientation of the legs as the surgical fastener is driven into tissue.

Referring to FIG. 6, in one embodiment, an insertion tool 260 is utilized for advancing the surgical fastener 220 described in FIGS. 5A-5E into tissue T for securing surgical mesh SM to the tissue T. In one embodiment, the insertion tool 260 has a base 262 and an insertion tine 264 projecting from a distal face 266 of the base 262. In one embodiment, the insertion tine 264 is centrally located on the distal face 266 of the base 262. In other embodiments, the base may have additional insertion tool openings and the insertion tool may have a similar number of insertion tines.

In one embodiment, the insertion tine 264 slides into the central opening 256 in the base 250 until the distal face 266 of the base 262 of the insertion tool 260 engages the proximal face 252 of the base 250 of the surgical fastener 220. The insertion tool 260 may drive the surgical fastener 220 through the surgical mesh SM and into the tissue T for securing the surgical mesh in place on the tissue. The distal face 266 of the base 262 and the tine 264 preferably control the orientation of the surgical fastener 220 as the legs 226 are driven into tissue T. The tissue engaging barbs 236 at the distal ends of the legs 226 desirably anchor the surgical fastener 220 in place within the tissue. The distal face 254 of the planar base 250 preferably engages the top surface of the surgical mesh SM for securing the mesh in place over the tissue T. A plurality of surgical fasteners may be passed through the surgical mesh SM for securing the mesh to the tissue.

In one embodiment, the surgical fastener may be made of absorbable and/or non-absorbable materials. Preferred absorbable materials include PDS, PDS/lactide-glycolide blends, PLA, etc. In one embodiment, each surgical fastener is sized to fit inside of a 5 mm outer diameter tube (typically trocar cannula dimension). The surgical fastener is fabricated by molding, however, with small modifications, other processes such as casting, stamping, and machining may be used. In one embodiment, the surgical fasteners may be extruded into a general shape, and then formed.

Although the present invention is not limited by any particular theory of operation, it is believed that providing an insertion tool with tines that engage insertion tool alignment surfaces on the legs of a surgical fastener will enhance stability and control of the surgical fastener when dispensing the surgical fastener from the distal end of the applicator instrument. In addition, the insertion force is provided closer to the distal end of the surgical fastener and not only at the proximal end of the surgical fastener as is the case with prior art systems. This feature (i.e. providing insertion force on the surgical fastener near the distal end of the fastener) may enable smaller and/or lower profile surgical fasteners to be used.

In one embodiment, the applicator instrument of the present invention may be used to repair of a defect, such as an inguinal hernia, located in inguinal tissue such as the inguinal floor. Generally, an inguinal hernia may be accessed through the iliacus muscle. As can be well appreciated, a network of vessels and nerves exist in the area of a typical inguinal hernia, which requires a surgeon to conduct a hernia repair with great skill and caution. For instance, in the transverse abdominis aponeurosis, an internal ring permits gastric vessels and Vas deferens to extend therethrough over an edge of inguinal ligament. A femoral canal is located near the Cooper's ligament and contains external iliac vessels and inferior epigastric vessels.

In many cases, the edge of the inguinal ligament and the Cooper's ligament serve as anatomical landmarks and support structures for supporting surgical fasteners such as those mentioned previously. The area containing the external iliac vessels and the Vas deferens may be commonly known as "the Triangle of Doom" to surgeons. Accordingly, care must be taken when performing dissection, suturing or fastening within this area.

A prosthetic or a mesh patch may be placed over the inguinal hernia. The mesh patch may have any desired configuration, structure or material. In one embodiment, the mesh patch may be made of PROLENE™ (a well-known polymer made of fibers) and preferably configured as mesh.

The mesh patch may be placed over the inguinal hernia for providing a sufficient barrier to internal viscera (not shown) of the abdomen which would otherwise have a tendency to protrude through the inguinal hernia and cause the patient a great deal of pain and discomfort. After the mesh patch has been placed onto the inguinal floor, the mesh patch is ready for attachment to the inguinal floor. The surgical fasteners disclosed herein are desirably utilized for attaching the mesh to the inguinal floor.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A surgical fastener for anchoring medical devices to tissue comprising:
   first and second legs lying in a first plane;
   third and fourth legs lying in a second plane that is orthogonal with the first plane;
   a bridge interconnecting proximal ends of said legs for forming a closed end of said surgical fastener;
   each said leg having the proximal end, a distal end, and an insertion tip with a distal point located at the distal end of said leg, wherein said bridge has an outer perimeter, and wherein said insertion tips at the distal ends of said legs extend outside the outer perimeter of said bridge;
   each said leg having an insertion tool alignment guide formed in an outer surface of said leg that extends from the proximal end to the distal end of said leg and along a longitudinal axis that is aligned with said distal point of said insertion tip, wherein said insertion tool alignment guide terminates at an insertion tool seating surface that is proximal to said distal point of said insertion tip.

2. The surgical fastener as claimed in claim 1, wherein each said leg comprises a tissue engaging barb projecting toward the proximal end of said leg and outwardly away from said leg.

3. The surgical fastener as claimed in claim 2, wherein said tissue engaging barb projects proximally from a proximal end of said insertion tip at the distal end of said leg.

4. The surgical fastener as claimed in claim 1, wherein each said insertion tip has a proximal end with said insertion tool seating surface facing toward the proximal end of said leg, wherein said insertion tool seating surface is aligned with said insertion tool alignment guide and said distal point of said insertion tip.

5. The surgical fastener as claimed in claim 4, wherein said insertion tool seating surface defines a distal-most end of said insertion tool alignment guide.

6. The surgical fastener as claimed in claim 1, wherein said insertion tip extends along an axis that is coaxial with the longitudinal axis of said insertion tool alignment guide.

7. The surgical fastener as claimed in claim 6, wherein the longitudinal axis of said insertion tool alignment guide intersects said distal point of said insertion tip.

8. The surgical fastener as claimed in claim 1, wherein said surgical fastener is absorbable.

9. The surgical fastener as claimed in claim 1, wherein said insertion tool alignment guides formed in the outer surfaces of said first and second legs face away from one another, and wherein said insertion tool alignment guides formed in the outer surfaces of said third and fourth legs face away from one another.

10. The surgical fastener as claimed in claim 1, wherein each said insertion tool alignment guide comprises a groove.

11. The surgical fastener as claimed in claim 10, wherein said grooves formed in the outer surfaces of said first and second legs face away from one another, and wherein said grooves formed in the outer surfaces of said third and fourth legs face away from one another.

12. The surgical fastener as claimed in claim 1, wherein said legs have a length of about 1-4mm.

13. A surgical fastener for anchoring medical devices to tissue comprising:
    first and second legs lying in a first plane;
    third and fourth legs lying in a second plane that is orthogonal with the first plane;
    a bridge interconnecting proximal ends of said first, second, third and fourth legs for forming a closed end of said surgical fastener;
    each said leg having the proximal end, a distal end, an outer surface that extends between the proximal and distal ends, and an insertion tip with a distal point located at the distal end of each said leg, wherein said bridge has an outer perimeter, and wherein said insertion tips at the distal ends of said legs extend outside the outer perimeter of said bridge;
    each of said first, second, third and fourth legs having an insertion tool alignment guide formed in the outer surface of each said leg that extends from the proximal end to the distal end of each said leg and along a longitudinal axis that is aligned with said distal point of said insertion tip, wherein said insertion tool alignment guide terminates at an insertion tool seating surface that is proximal to said distal point of said insertion tip.

14. The surgical fastener as claimed in claim 13, wherein said insertion tool alignment guides formed in the outer surfaces of said first and second legs face away from one another, and wherein said insertion tool alignment guides formed in the outer surfaces of said third and fourth legs face away from one another.

15. The surgical fastener as claimed in claim 14, wherein said insertion tool alignment guides formed in the outer surfaces of said legs comprise grooves.

16. The surgical fastener as claimed in claim 15, wherein said grooves formed in the outer surfaces of said first and second legs face away from one another, and wherein said grooves formed in the outer surfaces of said third and fourth legs face away from one another.

17. The surgical fastener as claimed in claim 13, wherein each said leg comprises a tissue engaging barb projecting toward the proximal end of said leg and outwardly away from said leg, and wherein said tissue engaging barb projects proximally from a proximal end of said insertion tip at the distal end of said leg.

18. The surgical fastener as claimed in claim 13, wherein each said insertion tip has a proximal end with said insertion tool seating surface facing toward the proximal end of said leg, wherein said insertion tool seating surface is aligned with said insertion tool alignment guide and said distal point of said insertion tip.

19. The surgical fastener as claimed in claim 18, wherein said insertion tool seating surface defines a distal-most end of said insertion tool alignment guide.

20. The surgical fastener as claimed in claim 13, wherein said insertion tip extends along an axis that is coaxial with the longitudinal axis of said insertion tool alignment guide, and wherein the longitudinal axis of said insertion tool alignment guide intersects said distal point of said insertion tip.

21. The surgical fastener as claimed in claim 13, wherein said legs have a length of about 1-4mm.

* * * * *